United States Patent [19]

Haag et al.

[11] 4,070,407

[45] Jan. 24, 1978

[54] ALKYLATION/TRANSALKYLATION IN PRESENCE OF CRYSTALLINE ALUMINOSILICATE CATALYST

[75] Inventors: Werner O. Haag, Trenton; David H. Olson, Pennington, both of N.J.

[73] Assignee: Mobil Oil Corporation, New York, N.Y.

[21] Appl. No.: 580,864

[22] Filed: May 27, 1975

Related U.S. Application Data

[63] Continuation-in-part of Ser. No. 449,315, March 8, 1974, abandoned.

[51] Int. Cl.² ............................ C07C 3/52; C07C 3/62
[52] U.S. Cl. ............................ 260/671 R; 260/672 T
[58] Field of Search ............ 260/671 R, 671 C, 672 T

[56] References Cited

U.S. PATENT DOCUMENTS

| 3,562,345 | 2/1971 | Mitsche | 260/672 |
| 3,668,264 | 6/1972 | Alley | 260/671 |
| 3,702,886 | 11/1972 | Arqauer et al. | 423/328 |
| 3,751,504 | 8/1973 | Keown et al. | 260/672 |
| 3,845,150 | 10/1974 | Yan et al. | 260/473.5 |
| 3,907,915 | 9/1975 | Chang et al. | 260/671 |
| 3,957,621 | 5/1976 | Bonacci et al. | 208/60 |
| 3,965,207 | 6/1976 | Weinstein | 260/671 M |
| 3,992,466 | 11/1976 | Plank et al. | 423/328 |

OTHER PUBLICATIONS

Wise et al., The American Mineralogist, vol. 54, May--June, 1969, pp. 887, 894 relied on.

*Primary Examiner*—C. Davis
*Attorney, Agent, or Firm*—Charles A. Huggett; Dennis P. Santini

[57] ABSTRACT

A process is provided for alkylation or transalkylation of aromatic hydrocarbons by contacting same with an alkylating or transalkylating agent in a reaction zone maintained under alkylation/transalkylation effective conditions and in the presence of a catalyst comprising a crystalline aluminosilicate zeolite characterized by a unique X-ray diffraction pattern, said catalyst under said conditions being capable of affording a high and selective yield of desired alkylaromatic product while maintaining excellent aging properties.

36 Claims, No Drawings

ALKYLATION/TRANSALKYLATION IN PRESENCE OF CRYSTALLINE ALUMINOSILICATE CATALYST

CROSS-REFERENCE TO RELATED APPLICATION

This is a continuation-in-part of application Ser. No. 449,315, filed Mar. 8, 1974, and now abandoned.

BACKGROUND OF THE INVENTION

1. Field of the Invention

This invention is directed to the alkylation or transalkylation of aromatic hydrocarbons including aromatic hydrocarbons containing a non-polar substituent, e.g., benzene or toluene, with an alkylating or transalkylating agent, e.g. an olefin or a polyalkylaromatic hydrocarbon, wherein the alkylation or transalkylation is performed in the presence of a zeolite characterized by long catalyst life, being capable of affording high selectivity to desired products, e.g. alkylaromatics, and which is easily and effectively regenerated, when necessary, without substantial loss in activity.

2. Description of the Prior Art

Alkylation of aromatic hydrocarbon compounds employing certain crystalline aluminosilicate zeolite catalysts is known in the art. For instance, U.S. Pat. No. 3,251,897 describes liquid phase alkylation in the presence of crystalline aluminosilicates such as faujasite, heulandite, clinoptilolite, mordenite, dachiardite, zeolite X and zeolite Y. The temperature of such alkylation procedure does not exceed 600° F for use of any of the aluminosilicates as catalyst.

Also, U.S. Pat. No. 2,904,607 shows alkylation of hydrocarbon compounds in the presence of certain crystalline aluminosilicate zeolites. The zeolites described for use in this patent are crystalline metallic aluminosilicates, such as, for example, magnesium aluminosilicate. U.S. Pat. No. 3,562,345 shows transalkylation of toluene over a zeolite catalyst typified by mordenite, e.g. Zeolon (see comparative examples hereinafter presented). U.S. Pat. No. 3,668,264 shows alkylation of aromatic hydrocarbons over several synthetic and naturally occurring zeolites, not including synthetic ZSM-35 or ZSM-38 zeolites. One naturally occurring zeolite mentioned as suitable in the latter patent is ferrierite (see comparative examples hereinafter presented).

U.S. Pat. No. 3,631,120 and 3,641,177 describe a liquid phase process for alkylation of aromatic hydrocarbons with olefins in the presence of certain zeolites. U.S. Pat. No. 3,631,120 discloses use of an ammonium exchanged, calcined zeolite having a silica to alumina mole ratio of between 4.0 and 4.9. U.S. Pat. No. 3,641,177 discloses use of a zeolite catalyst activated in a particular manner.

Unfortunately, while many of the crystalline aluminosilicate catalysts proposed for such alkylation methods provide satisfactory initial yields of desired products, for the most part, their catalytic aging properties are not sufficiently good enough to warrant commercial application. Hence, it is of advantage to provide a satisfactory process for alkylating or transalkylating aromatic hydrocarbons, depending upon whether an alkylating or transalkylating agent is employed, using a crystalline aluminosilicate zeolite catalyst which has improved aging properties, i.e., maintains alkylation or transalkylation in high yield over a long, commercially attractive period of time, heretofore lacking in the art.

SUMMARY OF THE INVENTION

This invention contemplates a process for effecting alkylation or transalkylation of aromatic hydrocarbons, including aromatic hydrocarbons containing a non-polar substituent, which comprises contacting the aromatic hydrocarbon charge with an alkylating agent or a transalkylating agent under conditions effective for accomplishing said alkylation or transalkylation including a reactor inlet temperature between about 100° F and about 1200° F, depending upon whether the process is alkylation or transalkylation, as distinguished hereinafter, a pressure between atmoshperic and 3,000 psig, employing a mole ratio of aromatic hydrocarbon to alkylating agent or transalkylating agent in the approximate range of 1:3 to 20:1 and a total feed weight hourly space velocity between about 0.5 and about 1,000, in the presence of a catalyst comprising a crystalline aluminosilicate zeolite e.g., ZSM-35 or ZSM-38, characterized by a unique specified X-ray powder diffraction pattern. The above weight hourly space velocity is based upon the weight of crystalline aluminosilicate.

The crystalline aluminosilicate zeolites useful as a catalyst in the process of this invention are represented by the general formula, expressed in terms of mole ratios of oxides in the anhydrous state as follows:

$$(0.3-2.5)R_2O : (0-0.8)M_2O : Al_2O_3 : > 8\ SiO_2$$

wherein R is an organic nitrogen-containing cation and M is an alkali metal cation, or the thermal decomposition product thereof.

DESCRIPTION OF SPECIFIC EMBODIMENTS

The ZSM-35 zeolite composition (described fully in copending U.S. Patent application Ser. No. 528,061, filed Nov. 29, 1974, the disclosure of which is incorporated herein by reference) has its own characteristic X-ray diffraction pattern, the values of which are set forth in Table 1, hereinafter.

The ZSM-35 composition can also be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from ethylenediamine or pyrrolidine and M is an alkali metal cation. It will be noticed that the ratio of $R_2O$ to $Al_2O_3$ may exceed unity in this material due to the occlusion of excess organic species ($R_2O$) within the zeolite pores.

ZSM-35 can further be characterized by its sorptive capacity at 90° C, as will be hereinafter established.

In a preferred synthesized form, the zeolite ZSM-35 has a formula, in terms of mole ratios of oxides and in the anhydrous state, as follows:

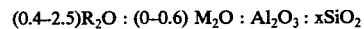

$$(0.4-2.5)R_2O : (0-0.6)\ M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The ZSM-38 zeolite composition (described fully in copending U.S. Patent application Ser. No. 560,412, filed Mar. 20, 1975, the disclosure of which is incorporated herein by reference) has its own characteristic X-ray diffraction pattern, the values of which are set forth in Table 2, hereinafter.

The ZSM-38 composition can also be identified, in terms of mole ratios of oxides and in the anhydrous state, as follows:

$$(0.3-2.5)R_2O : (0-0.8)M_2O : Al_2O_3 : > 8 SiO_2$$

wherein R is an organic nitrogen-containing cation derived from a 2-(hydroxyalkyl)trialkylammonium compound and M is an alkali metal cation. It will be noticed that the ratio of $R_2O$ to $Al_2O_3$ may exceed unity in this material due to the occlusion of excess organic species ($R_2O$) within the zeolite pores.

ZSM-38 can further be characterized by its sorptive capacity at 90° C, as will be hereinafter established.

In a preferred synthesized form, zeolite ZSM-38 has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The original cations of the as synthesized ZSM-35 and ZSM-38 can be replaced in accordance with techniques well known in the art, at least in part, by ion exchange with other cations. Preferred replacing cations are those which render the zeolite catalytically active, especially for hydrocarbon conversion such as the alkylation/transalkylation process of the present invention. These include hydrogen, rare earth metals, aluminum, metals of Groups IIA, IIIB, IVB, VIB, VIII, IB, IIB, IIIA, IVA. Non-limiting examples of such replacing cations which are metals are Mn, Ca, Mg, Zn, Cd, Pt, Pd, Ni, Co, Ti, Sn and Fe.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 150° F to about 600° F and thereafter may be calcined in air or other inert gas at temperatures ranging from about 500° F to 1500° F for periods of time ranging from 1 to 48 hours or more to produce a catalytically-active thermal decomposition product thereof.

The synthetic ZSM-35 zeolite possesses a definite distinguishing crystalline structure whose X-ray diffraction pattern shows substantially the significant lines set forth in Table 1. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3-11.5A. This very weak line, however, is determined not to be a significant line for ZSM-35.

TABLE 1

| d(A) | I/Io |
|---|---|
| 9.6 ± 0.20 | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium-Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak-Medium |
| 3.14 ± 0.06 | Weak-Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

The synthetic ZSM-38 possesses a definite distinguishing crystalline structure whose X-ray diffraction pattern shows substantially the significant lines set forth in Table 2. Again it is observed that this X-ray diffraction pattern (with respect to significant lines) is similar to that of natural ferrierite with a notable exception being that natural ferrierite patterns exhibit a significant line at 11.33A.

TABLE 2

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 5.0 ± 0.10 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

The values of Tables 1 and 2 were determined by standard technique. The radiation was the K-alpha doublet of copper and a scintillation counter spectrometer with a strip chart pen recorder was used. The peak heights, I, and the positions as a function of 2 times theta, where theta is the Bragg angle, were read from the spectrometer chart. From these, the relative intensities, 100 I/Io, where Io is the intensity of the strongest line or peak, and d (obs.), the interplanar spacing in Angstrom units, corresponding to the recorded lines, were calculated. It should be understood that the X-ray diffraction pattern data of Tables 1 and 2 are characteristic of all species of ZSM-35 and ZSM-38 compositions, respectively. Ion exchange of the sodium ion with cations reveals substantiallly the same pattern with some minor shifts in interplaner spacing and variation in relative intensity. Other minor variations can occur depending on the silicon to aluminum ratio of the particular sample, as well as if it has previously been subjected to thermal treatment.

A further characteristic of ZSM-35 and ZSM-38 is their sorptive capacity proving said zeolites to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 and ZSM-38 (after calcination at 600° C) is less than 10, whereas that ratio for the natural ferrierite is substantially greater than 10, for example, as high as 34 or higher.

Synthetic ZSM-35 and ZSM-38 can be used in the present invention either in the organic nitrogen-containing and alkali metal containing from, the alkali metal form and hydrogen form or other univalent and multi-valent cationic form. They can also be used in intimate combination with a hydrogenating component such as tungsten, vanadium, molybdenum, rhenium, nickel, cobalt, chromium, manganese, or a noble metal such as platinum or palladium. Such components can be exchanged into the composition, impregnated therein or physically intimately admixed therewith. Such components can be impregnated in or on to the present zeolite compositions, by, for example, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

As prepared, R can be one or more of a variety of organic nitrogen-containing cations present in quantity of not less than 40% of the whole, non-limiting examples of which include those cations derived from pyrrolidine, 2-(Hydroxyalkyl) trialkylammonium compounds, such as, for example, 2-(hydroxyethyl) triethylammonium chloride, and ethylenediamine. Non-limiting examples of the 2-(hydroxyalkyl) trialkylammonium compounds useful in this invention for R include the halides, e.g., fluorides, chlorides and bromides, the sulfates, the acetates, the nitrates and others. Of course, when the zeolite is ZSM-38 as prepared, R is a 2-(hydroxyalkyl) trialkylammonium cation. When the zeolite is ZSM-35, as prepared, R is the cation derived from ethylenediamine or pyrrolidine.

Also, M can be one or more of a variety or alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali metal ions include sodium and potassium.

Synthetic ZSM-35 and ZSM-38, when employed as the catalyst in the present process, should be dehydrated at least partially. This can be done by heating to a temperature in the range of 200° to 600° C in an inert atmosphere, such as air, nitrogen, etc. and at atmospheric or subatmospheric pressure for between 1 and 48 hours. Dehydration can also be performed at lower temperatures merely by placing the catalyst in a vacuum, but a longer time is required to obtain a sufficient amount of dehydration.

The zeolites for use in the present invention can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

|  | Broad | Preferred |
| --- | --- | --- |
| $R^+$ | 0.2–1.0 | 0.3–0.9 |
| $\overline{R^+ + M^+}$ | | |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived, in the case of ZSM-35, from ethylenediamine, pyrrolidine or, in the case of ZSM-38, from a 2-(hydroxyalkyl)trialkylammonium compound, and M is an alkali metal ion, and maintaining the mixture until crystals of the zeolite are formed. The quantity of OH- in the above ranges is calculated only from the inorganic sources of alkali without any organic base contribution. Thereafter, the crystals are separated from the liquid and recovered. Typical reaction conditions consist of heating the foregoing reaction mixture to a temperature of from about 90° F to about 400° F for a period of time of from about 6 hours to about 100 days. A more preferred temperature range is from about 150° F to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing.

The crystalline product is dried, e.g. at 230° F for from about 8 to 24 hours. Of course, milder conditions may be employed if desired, e.g. room temperature under vacuum.

The composition for the synthesis of synthetic ZSM-35 and ZSM-38 can be prepared utilizing materials which can supply the appropriate oxide. Such compositions include aluminates, alumina, silicates, silica hydrosol, silica gel, silicic acid and hydroxides. It will be understood that each oxide component utilized in the reaction mixture for preparing the present zeolites can be supplied by one or more essential reactants and they can be mixed together in any order. For example, any oxide can be supplied by an aqueous solution, sodium hydroxide or by an aqueous solution of a suitable silicate; the organic nitrogen-containing cation can be supplied by a compound of that cation, such as, for example, the hydroxide or a salt, as well as by the indicated amines. The reaction mixture can be prepared either batchwise or continuously. Crystal size and crystallization time will vary with the nature of the reaction mixture employed.

The ZSM-35 and ZSM-38 zeolites have an exceptionally high degree of thermal stability thereby rendering them particularly effective for use in processes involving elevated temperatures. In this connection, they appear to be some of the most stable zeolites known to date. However, it has been found that the process of this invention may be carried out at reactor bed temperatures not in excess of about 1200° F. At reactor bed temperatures substantially above 1200° F, products of the present process may undergo degradation resulting in the loss of desired products and reactants. Undesirable residues may be formed from the degradation reactions. In addition, olefins used as alkylating agents may polymerize with themselves or other reactants to form resinous compounds within the reaction zone. These resinous compounds together with the degradation products may lead to the formation of coke-like deposits on the active surfaces of the catalyst. As a result, these deposits rapidly destroy the high activity of the catalyst and greatly shorten its effective life. Such undesirable effects are obviated under the conditions and with the catalyst employed in the present process.

Of particular importance for a practical alkylation or transalkylation process is that the catalyst has a long useful life and does not deactivate rapidly. In this respect it has been found that the present catalyst (i.e., ZSM-35 or ZSM-38) has an extraordinary resistance to deactivation not found by prior art catalysts such as faujasite or mordenite zeolite catalysts. With the latter catalysts, many undesirable side reactions always accompany the catalytic alkylation or transalkylation of aromatic hydrocarbons.

While the exact reason for this unusual behavior is not fully established, it is believed to result from the specific structure and dimensions of the pores of the ZSM-35 and ZSM-38 zeolites, which have smaller cross-sectional dimensions than those of the previously mentioned zeolites (e.g., faujasite and mordenite) but are still large enough to admit aromatic molecules. ZSM-35 and ZSM-38 zeolites differ in this regard from the catalytically inactive small pore zeolites A and erionite. In addition, the high $SiO_2/Al_2O_3$ ratio of ZSM-35 and ZSM-38 zeolites also is believed to be a contributing factor to its long catalyst life.

The aluminosilicate prepared for use in the instant invention may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

For use herein, it may be desired to incorporate the zeolite with another material resistant to the temperatures and other conditions employed in the present processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides.

In addition to the foregoing materials mentioned, the zeolite catalyst for use herein can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline aluminosilicate and inorganic oxide gel matrix vary widely with the crystalline aluminosilicate content ranging from about 1 to about 99 percent by weight and more usually in the range of about 5 to about 80 percent by weight of the composite.

Exemplary of the hydrocarbons which may be alkylated or transalkylated by the process of this invention, depending upon whether an alkylating agent or a transalkylating agent is employed, are aromatic compounds such as benzenes, naphthalenes, anthracenes, and the like and substituted derivatives thereof; and alkyl substituted aromatics, e.g. toluene, xylene, and homologs thereof. In general, non-polar substituent groups may be attached to the nucleus of the aromatic ring including, by way of non-limiting example:

Alkyl ($-C_nH_{(2n+1)}$), such as methyl, ethyl, propyl and tert-butyl;

Cycloalkyl ($-C_nH_{(2n-1)}$), such as cyclopentyl and cyclohexyl; and

Aryl, such as phenyl and naphthyl.

In accordance with this invention and when alkylation is to be accomplished, the preferred alkylating agents are olefins such as, for example, ethylene, propylene, butene, decene, dodecene, as well as formaldehyde, alkyl halides and alcohols; the alkyl portion thereof having from 1 to 24 carbon atoms. Numerous other acyclic compounds having at least one reactive alkyl radical may be utilized as alkylating agents.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene and ethyltoluene.

It is interesting to note in regard to the utility of the ZSM-35 and ZSM-38 zeolites as the catalyst for use herein that it has a one-dimensional channel system of about 6 Angstrom Units maximum, that is about 1 Angstrom Unit smaller than that of ZSM-5 (U.S. Pat. No. 3,702,886) and considerably smaller than those of many other zeolites known in the art to have catalytic activity for alkylation and transalkylation reactions. In view of this, the excellent utility of the ZSM-35 and ZSM-38 zeolites with respect to such reactions is unexpected.

Operating conditions employed in the process of the present invention are critical and will be dependent, at least in part, on the specific alkylation or transalkylation reaction being effected. Such conditions as temperature, pressure, space velocity and molar ratio of the reactants and the presence of inert diluents will have important affects on the process.

When alkylation is the process conducted according to this invention and the alkylating agent is an olefin, the temperature of the reaction is preferably within the range of about 100° F to about 950° F, with a particularly preferred temperature range of about 400° F to about 900° F. When the alkylating agent is an alcohol, the preferred reaction temperature is within the range of about 400° F to about 1200° F, with a particularly preferred temperature range of about 700° F to about 1125° F.

When transalkylation is the process conducted according to the invention, the reaction temperature is preferably within the range of about 650° F to about 1100° F, with a particularly preferred temperature range of about 750° F to about 950° F.

Preferred reaction pressure in either alkylation or transalkylation according to the present invention is from about 25 psig to about 800 psig. In any case, the preferred weight hourly space velocity is within the range of about 1 to about 20.

The process of this invention is conducted such that alkylation or transalkylation of an aromatic hydrocarbon compound, exemplified by benzene, with an alkylating agent, such as an olefin, exemplified by ethylene, or a transalkylation agent, such as a polyalkylaromatic hydrocarbon, exemplified by 1,3,5-trimethylbenzene, is carried out by contact in a reaction zone, such as, for example, a fixed bed of catalyst, under alkylation or transalkylation effective conditions.

For alkylation, the alkylatable aromatic compound and alkylating agent are desirably fed to a first stage at an appropriate mole ratio of one to the other. The feed to such first stage is heated. After some reaction takes place, such as, for example, when about 80 percent of the alkylating agent is consumed, the effluent of the first stage is cooled to remove heat of reaction and more alkylating agent is added (second stage) to maintain the mole ratio of aromatic compound to alkylating agent within the range established for the first stage. A plurality of reaction stages are possible for the process of this invention. It is generally desirable to provide cooling between reactor stages.

Considering, for example, alkylation of benzene with ethylene, the first stage mole ratio of benzene to ethylene may be in the range of about 1:3 to about 20:1. The first stage feed is heated to a reactor inlet temperature within the range of about 100° F to about 1200° F at a pressure within the range of about atmospheric to about 3000 psig. Preferred inlet temperatures fall within the range of about 100° F to about 950° F and preferred pressures fall within the range of about 25 psig to about 800 psig. The repeating of reaction staging is carried out while maintaining an overall aromatic hydrocarbon, e.g., benzene, to alkylating agent, e.g., ethylene, mole ratio of about 1:3 to about 20:1, with a preferred range of about 1:2 to about 16:1. As the reaction proceeds through the stages, the aromatic to alkylating agent mole ratio increases.

In conducting a transalkylation reaction in accordance with the present invention, a single stage reactor is usually sufficient. Suitable mole ratios of aromatic hydrocarbon to transalkylating agent range from 1:3 to 20:1, and preferably range from 1:2 to 5:1. Preferred reaction pressures in this case fall within the range of about 25 psig to about 800 psig.

It is noted that disproportionation is a special case of transalkylation in which the alkylatable aromatic hydrocarbon and the transalkylating agent is the same compound, for example when toluene serves as the donor and acceptor of a transferred methyl group to produce benzene and xylene. It should be understood that the term transalkylation as used herein includes the special case of disproportionation.

It is also noted that extremely high total feed space velocities are possible in the process of this invention, i.e., up to 1,000 pounds total feed/hour-pound crystalline aluminosilicate. An important factor in the present process is, however, the weight hourly space velocity (WHSV) of the alkylating agent or transalkylating agent. The alkylating agent or transalkylating agent WHSV to each of any alkylation or transalkylation reactor stages is maintained between about 1 and about 10 pounds agent/hour-pound crystalline aluminosilicate. The most desirable alkylating agent or transalkylating agent WHSV is within the range of about 2 to about 6 pounds agent/hour-pound crystalline aluminosilicate. When the WHSV is maintained within the above limits, an economical cycle between regenerations of catalyst exists.

This process, of course, can be conducted within either a fixed or fluidized catalyst bed, with attendant benefits in either circumstance readily attainable.

The following examples will serve to illustrate the process of the invention, without unduly limiting same.

EXAMPLE 1

Illustrating preparation of synthetic zeolite ZSM-35, a first solution comprising 33.0 grams sodium aluminate (41.8% $Al_2O_3$, 31.6% $Na_2O$ and 24.9% $H_2O$), 870 grams $H_2O$ and 3.4 grams NaOH (50% solution with water) was prepared. The organic material pyrrolidine was added to the first solution in 182.0 gram quantity to form a second solution. Thereupon 824 grams colloidal silica (29.5% $SiO_2$ and 70.5% $H_2O$) was added to the second solution and mixed until a homogeneous gel was formed. This gel was composed of the following components in mole ratios:

| | |
|---|---|
| $\dfrac{R^+}{R^+ + M^+}$ | 0.87, wherein M is sodium and $R^+$ is the pyrrolidine ion. |
| $OH^-$ | 0.097 (Not including any contribution of $OH^-$ from pyrrolidine) |
| $SiO_2$ | |
| $H_2O$ | 202 (Not including any contribution of $OH^-$ from pyrrollidine) |
| $\dfrac{OH^-}{SiO_2}$ | |
| $Al_2O_3$ | 29.0 |

The mixture was maintained at 275° F for 17 days, during which time crystallization was complete. The product crystals were filtered out of solution and water washed for approximately 16 hours on continuous wash line.

X-ray analysis of the crystalline product proved the crystals to have a diffraction pattern as shown in Table 1.

Chemical analysis of the crystalline product led to the following compositional figures:

| Composition | Mole Ratio on $Al_2O_3$ Basis |
|---|---|
| $N_2O$ | 1.23 |
| $Na_2O$ | 0.08 |
| $SiO_2$ | 29.00 |

Physical analysis of the crystalline product of Example 1 calcined 16 hours at 1000° F showed it to have a surface area of 349 m²/g and adsorption tests produced the following results:

| Adsorption | Wt. % |
|---|---|
| Cyclohexane | 2.1 |
| n-Hexane | 8.2 |
| Water | 11.0 |
| n-Hexane/2-methylpentane (90° C) = 1.8 | |

EXAMPLE 2

Illustrating a preparation of ZSM-38, a first solution was prepared comprising 34.4g sodium silicate (28.8% $SiO_2$, 8.9% $Na_2O$ and 62.2% $H_2O$), 2.4g sodium aluminate (44.7% $Al_2O_3$, 31.3% $Na_2O$ and 24.0% $H_2O$), 9.7g NaOH and 76.4g water. A second solution was prepared by first mixing 23.74g $Al_2(SO_4)_3 \cdot 14\ H_2O$, 12.5g $H_2SO_4$ and 75.0g water and then adding to that mixture 135.0g of the sodium silicate. At this point, the second solution was added to the first solution to provide a gel which was mixed until homogeneous and aged at 99° C for 1-2 hours. The solid which formed was filtered out and the filtrate was discarded. A third solution, made up of 18.72g of 2-(hydroxyethyl) trimethylammonium chloride, 10.0g of 10% NaOH solution and 20.0g water, was then added to the above solid and the resulting mixture was mixed until homogeneous and crystallized (99° C for 83 days).

The crystallization mixture was comprised of the following components in mole ratios:

| | |
|---|---|
| $\dfrac{R^+}{R^+ + M^+}$ | 0.31, wherein M is sodium and R is [(CH$_3$)$_3$-n-CH$_2$CH$_2$OH] |
| $\dfrac{OH^-}{SiO_2}$ | 0.36 |
| $\dfrac{H_2O}{OH^-}$ | 52.2 |
| $\dfrac{SiO_2}{Al_2O_3}$ | 16.4 |

The crystalline product was filter separated, water washed and X-ray analyzed. The X-ray analysis showed the crystalline product of this example to have the diffraction pattern shown below:

X-RAY DIFFRACTION PATTERN OF ZSM-38 OF EXAMPLE 2

| 2 Times Theta | d(A) | I/Io |
|---|---|---|
| 9.02 | 9.80 | 45 |
| 9.70 | 9.12 | 29 |
| 11.10 | 7.97 | 2 |
| 12.50 | 7.08 | 34 |
| 13.25 | 6.68 | 34 |
| 14.70 | 6.03 | 15 |
| 15.20 | 5.83 | 11 |
| 17.75 | 5.00 | 13 |
| 18.77 | 4.73 | 11 |
| 20.33 | 4.37 | 7 |
| 21.00 | 4.23 | 5 |
| 22.15 | 4.01 | 82 |
| 23.35 | 3.81 | 68 |
| 24.10 | 3.69 | 23 |
| 24.97 | 3.57 | 100 |
| 25.40 | 3.51 | 100 |
| 26.70 | 3.34 | 26 |
| 28.17 | 3.17 | 48 |
| 28.97 | 3.08 | 24 |
| 29.76 | 3.00 | 17 |
| 30.60 | 2.921 | 29 |
| 32.75 | 2.734 | 5 |
| 33.73 | 2.657 | 11 |
| 34.55 | 2.596 | 6 |
| 36.00 | 2.495 | 7 |
| 36.90 | 2.436 | 3 |
| 37.87 | 2.376 | 4 |
| 38.60 | 2.332 | 4 |
| 39.70 | 2.270 | 2 |
| 42.50 | 2.127 | 4 |
| 43.80 | 2.067 | 2 |
| 44.50 | 2.036 | 7 |

Chemical analysis of the product of this example provided the following compositional figures:

| Composition | Wt. % | Mole Ratio on Al$_2$O$_3$ Basis |
|---|---|---|
| N | 1.35 | — |
| Na | 2.60 | — |
| Al$_2$O$_3$ | 12.60 | 1.0 |
| SiO$_2$ | 83.5 | 11.85 |
| N$_2$O | — | 0.53 |
| Na$_2$O | — | 0.48 |
| H$_2$O | — | 5.28 |

Physical analysis of the product of this example indicated that the surface area of the crystals after calcination at 1000° F for 16 hours was 372 m²/g. Adsorption tests provided the following data:

| Adsorption | Wt. % |
|---|---|
| Cyclohexane | 5.2 |
| n-Hexane | 7.2 |
| Water | 11.2 |
| n-Hexane/2-methyl-pentane (90° C) = | 1.89 |

EXAMPLE 3

In yet another illustration of the preparation of ZSM-38, a first solution was prepared comprising 103.2 grams sodium silicate (as defined in Example 2), 7.2 grams sodium aluminate (as defined in Example 2), 29.1 grams sodium hydroxode and 229.2 grams water. A second solution was prepared by first mixing 71.22 grams Al$_2$(SO$_4$)$_3$.14H$_2$O, 37.5 grams H$_2$SO$_4$ and 225 grams water and then adding to that mixture 405 grams of the sodium silicate. The second solution was then added to the first solution and the resultant gel was mixed until homogeneous and aged at 99° C for 1-2 hours. The solid which formed was then filtered out of solution and the filtrate was discarded. A third solution, made up of 56.2 grams 2-(hydroxyethyl) trimethylammonium chloride, 30.0 grams of 10% sodium hydroxide solution and 60.0 grams water, was then added to the above solid and the resulting mixture was mixed until homogeneous and crystallized (99° C for 70 days).

The crystallization mixture was comprised of the following components in moles or measurements in mole ratios:

| | |
|---|---|
| $\dfrac{R^+}{R^+ + M^+}$ | 0.31, wherein M and R are as defined in Example 2 |
| $\dfrac{OH^-}{SiO_2}$ | 0.35 |
| $\dfrac{H_2O}{OH^-}$ | 52.2 |
| $\dfrac{SiO_2}{Al_2O_3}$ | 16.1 |

The crystalline product was filter separated, water washed and X-ray analyzed. The X-ray analysis showed the crystalline product of Example 3 to have the diffraction pattern of Table 2.

Chemical analysis of the product of Example 3 provided the following compositional figures:

| Composition | Wt. % | Mole Ratio on Al$_2$O$_3$ Basis |
|---|---|---|
| N | 1.41 | — |
| Na | 2.20 | — |
| Al$_2$O$_3$ | 11.6 | 1.0 |
| SiO$_2$ | 87.5 | 12.83 |
| N$_2$O | — | 0.77 |
| Na$_2$O | — | 0.42 |
| H$_2$O | — | 6.20 |

Physical analysis of the product of Example 3 calcined 16 hours at 1,000° F indicated that the surface area of the crystals was 403 m²/g. Adsorption tests provided the following data:

| Adsorption | Wt. % |
|---|---|
| Cyclohexane | 7.1 |
| n-Hexane | 7.1 |
| Water | 13.4 |
| n-Hexane/2-methyl- | |

| Adsorption | Wt. % |
|---|---|
| pentate (90° C) = | 2.70 |

EXAMPLE 4

Over a fixed bed of catalyst as prepared in Example 1 a feed of toluene was contacted with the alkylating agent methyl alcohol in the mole ratio of toluene to methyl alcohol of 2:1. The reactor inlet temperature was 450° F and the reactor pressure was maintained at 400 psig. The total feed weight hourly space velocity was 8 and the time of reaction was 4.9 hours. Table 3 lists the compositions of the liquid product in weight percent, conversion in weight percent and selectivity calculated as (weight percent xylene/weight percent conversion) x 100%.

EXAMPLE 5

The same catalyst from Example 4 was then tested (without regeneration) as in Example 4 for 14.7 hours with only the weight hourly space velocity change to 2. The results of this example also appear in Table 3.

EXAMPLE 6

The same catalyst from Example 5 was then tested (without regeneration) as in Example 4 for 1.9 hours with the temperature raised to 550° F and the weight hourly space velocity maintained at 8. The results of this example also appear in Table 3.

EXAMPLE 7

The catalyst from Example 6 was then tested (without regeneration) as in Example 4 for 1.7 hours with only the temperature changed to 650° F. The results of this example also appear in Table 3.

EXAMPLE 8

The catalyst from Example 7 was then tested (without regeneration) as in Example 4 for 1.6 hours with only the temperature changed to 750° F. The results of this example also appear in Table 3.

EXAMPLE 9

The catalyst from Example 8 was then tested (without regeneration) as in Example 8 for 2.7 hours with only the weight hourly space velocity changed to 4. The results of this example also appear in Table 3.

EXAMPLE 10

The catalyst from Example 9 was then tested (without regeneration) as in Example 6 for 16.3 hours with only the weight hourly space velocity changed to 2. The results of this example also appear in Table 3.

EXAMPLE 11

The catalyst from Example 10 was then tested (without regeneration) as in Example 7 for 5.9 hours with the reaction pressure maintained at 1 atmosphere and the weight hourly space velocity changed to 4. The results of this example also appear in Table 3.

EXAMPLE 12

The catalyst from Example 11 was then tested (without regeneration) as in Example 7 for 47.9 hours with only the weight hourly space velocity changed to 4. The results of this example also appear in Table 3.

TABLE 3

ALKYLATION OF TOLUENE WITH METHANOL OVER ZSM-35

| Example | Benzene | Toluene | Xylenes | p-Xylene | m-Xylene | o-Xylene | $C_9+$ | Weight percent[a] Conversion | Selectivity |
|---|---|---|---|---|---|---|---|---|---|
| 4 | 0 | 99.60 | 0.38 | 0.20 | | 0.18 | 0 | 0.4 | 95[b] |
| 5 | 0 | 99.00 | 0.91 | 0.21 | 0.21 | 0.45 | 0 | 1.0 | 91[b] |
| 6 | 0.01 | 93.06 | 5.97 | 1.54 | 1.35 | 3.08 | 0.86 | 6.94 | 86.0 |
| 7 | 0.24 | 75.72 | 16.20 | 3.79 | 8.75 | 3.66 | 7.64 | 24.3 | 66.7 |
| 8 | 1.33 | 65.97 | 21.36 | 5.22 | 11.31 | 4.83 | 10.93 | 34.0 | 62.8 |
| 9 | 1.73 | 67.31 | 20.70 | 4.99 | 11.22 | 4.50 | 9.85 | 32.7 | 63.3 |
| 10 | 0.04 | 95.27 | 3.81 | 1.94 | | 1.87 | 0.78 | 4.7 | 81.1 |
| 11 | 0.02 | 84.54 | 12.48 | 3.31 | 3.62 | 5.56 | 2.82 | 15.5 | 80.5 |
| 12 | 0.06 | 77.71 | 14.32 | 6.83 | | 7.49 | 7.19 | 22.3 | 64.2 |

[a]Conversion of toluene; maximum conversion possible is 50%
[b]Selectivity in mole percent xylene.

EXAMPLE 13

A 1.0 cc portion (0.63 gram) of the product crystalline zeolite ZSM-35 of Example 1 was placed in a glass reactor and heated from 75° F to 1000° F in flowing air (100 cc/minute) and held at 1000° F for one hour. An equimolar mixture of toluene and 1,2,4-trimethylbenzene was then passed over the catalyst at 950° F and atmospheric pressure. The weight hourly space velocity was maintained at 1.0. The results of this example appear in Table 4, hereinafter presented.

EXAMPLE 14

The experiment outlined in Example 13 was repeated, except that the temperature was 851° F and the weight hourly space velocity was maintained at 4.0. The results of this example are also listed in Table 4.

TABLE 4

TRANSALKYLATION OVER ZSM-35

| Example No. Product Analysis (Wt. %) | Feed | 13 | 14 |
|---|---|---|---|
| Benzene | | 5.0 | 1.3 |
| Toluene | 43.4 | 32.7 | 38.1 |
| p,m-Xylene | | 22.7 | 10.8 |
| o-Xylene | | 6.8 | 3.1 |
| Total Xylene | | 29.5 | 13.9 |
| TMB[a] | 56.6 | 29.3 | 45.5 |
| Other $C_9+$ | | 3.0 | 1.2 |
| Conversion[b] | | 71.5 | 33.4 |

[a]1,2,4-Trimethylbenzene.
[b]Conversion to xylenes (percent of equilibrium).

EXAMPLE 15

Propylene was bubbled through a 154° F benzene solution containing a quantity of the ZSM-35 zeolite prepared in Example 1 in the ratio of 10 grams of benzene per gram of zeolite catalyst. Cumene was produced at the hourly rate of 14 grams per 100 grams of zeolite ZSM-35 catalyst.

EXAMPLE 16

In order to compare the aging properties of the catalyst for use in the present process with the same properties of a commercially available catalyst used in the art for alkylation or transalkylation, a quantity of Zeolon 100H, a commercially available form of synthetic hydrogen-mordenite, was pretreated by heating through the range of 70° F to 1000° F over a 1.5 hour period followed by 1.0 hour at 1000° F. The heating was accomplished in the presence of dry air flowing at the rate of 100 cc/minute.

A quantity of the ZSM-35 zeolite as prepared in Example 1 and an equal quantity of the pretreated commercial catalyst were placed in identical reactors, each held at a temperature of 800° F while an equimolar mixture of toluene and 1,2,4-trimethylbenzene were passed therethrough at a weight hourly space velocity of 4.0. The results of this experiment are shown in Table 5. It is noted that conversion to xylenes with the commercial catalyst is quite high at the start of the experiment, but almost nil (0.8%) after 2.5 hours on stream. The catalyst for use in the present process is still providing a 19.3% conversion after 2.5 hours of the test.

TABLE 5

|  | ZSM-35 | Commercial Catalyst | ZSM-35 | Commercial Catalyst |
|---|---|---|---|---|
| Time on stream (hours) | 0.13 | 0.17 | 2.5 | 2.5 |
| Product Analysis (wt.%) |  |  |  |  |
| Benzene | 1.38 | 2.83 | 0.58 | 0 |
| Toluene | 36.77 | 28.68 | 39.55 | 43.91 |
| Xylene | 13.00 | 29.72 | 7.99 | 0.31 |
| TMB[a] | 47.61 | 35.53 | 51.08 | 55.67 |
| Other $C_9$+ | 1.17 | 3.08 | 0.74 | 0.09 |
| Conversion[b] | 31.50 | 72.00 | 19.30 | 0.8 |

[a]1,2,4-Trimethylbenzene
[b]Conversion to xylenes (percent of equilibrium).

EXAMPLE 17

A 100 gram quantity of naturally occurring ferrierite ore was made into the hydrogen cation-containing form (H-ferrierite) by ammonium exchanging said ore at 25° C, with stirring, as follows:

1. contacting the ore with 2.0 liters of 0.2 N $NH_4NO_3$ solution for 20 hours, filtering and washing with distilled water, then
2. contacting a second time with 2.0 liters of 4.0 N $NH_4NO_3$ solution for 69 hours, filtering and washing with distilled water, then
3. contacting a third time with 2.0 liters of 4.0 N $NH_4NO_3$ solution for 42 hours, filtering and washing with distilled water, and then
4. contacting a fourth time with 2.0 liters of 0.01 N $NH_4NO_3$ solution for 22 hours, filtering, washing with distilled water and drying.

The treated ferrierite ore was then calcined in air for 10 hours at 1000° F.

EXAMPLE 18

A 1.0 cc portion of the product crystalline zeolite ZSM-35 of Example 1 was placed in a glass reactor and heated from 75° F to 1000° F in flowing air (100 cc/minute) and held at 1000° F for one hour. An equimolar mixture of toluene and 1,2,4-trimethylbenzene was then passed over the catalyst at 800° F and atmospheric pressure. The weight hourly space velocity was maintained at 4.0. The results of this experiment appear in Table 6, hereinafter presented.

EXAMPLE 19

The experiment of Example 18 was repeated under identical conditions with the exception that the H-ferrierite prepared in Example 17 was used as catalyst in place of the ZSM-35. The results of this experiment appear in Table 6, below. It is apparent from comparison of the data obtained from the experiments of Examples 18 and 19 that a catalyst material of naturally occurring ferrierite is considerably less active than the ZSM-35 in the present process.

TABLE 6

TRANSALKYLATION OVER ZSM-35 AND ACTIVATED NATURAL FERRIERITE

| Example No. | Feed | 18 | 19 |
|---|---|---|---|
| Product Analysis (Wt. %) |  |  |  |
| Benzene |  | 0.8 | 0 |
| Toluene | 43.4 | 39.6 | 41.4 |
| Total Xylenes |  | 9.6 | 1.5 |
| TMB[a] | 56.6 | 49.0 | 56.5 |
| Other $C_9$+ |  | 0.9 | 0.6 |
| Conversion[b] |  | 23.3 | 3.6 |

[a]1,2,4-Trimethylbenzene.
[b]Conversion to xylenes (percent of equilibrium).

EXAMPLE 20

The experiment of Example 18 was repeated under identical conditions with the exception that the ZSM-35 catalyst used in Example 18 was replaced with a 1.0cc portion of the product crystalline zeolite ZSM-38 of Example 3. Transalkylation occurred to produce predominently xylenes and in addition a small amount of benzene and $C_9$ + material. Conversion in this experiment to xylenes was 57 weight percent (of equilibrium). When this result is compared with the 3.6 weight percent conversion obtained in Example 19, it is readily observed that a ZSM-35 or ZSM-38 zeolite can provide up to 1480 percent more transalkylation of aromatics than an activated natural ferrierite.

EXAMPLE 21

In this experiment, propylene was bubbled through a 154° F benzene solution containing a quantity of the ZSM-38 zeolite prepared in Example 3 in the ratio of 10 grams of benzene per gram of zeolite catalyst. Cumene was produced at the hourly rate of 95 grams per 100 grams of catalyst.

It will be noted from the examples of this invention that the alkylation or transalkylation of aromatic hydrocarbon compounds by contacting with the ZSM-35 or ZSM-38 catalysts provides substantial benefits over a similar process with other catalysts known in the art for alkylation or transalkylation. For example, and possibly the most important fact, ZSM-35 and ZSM-38 exhibit markedly improved aging properties. Instead of cycle periods of a few hours as has been the practice of the prior art, a cycle of days or weeks is possible.

It will be appreciated that the examples set forth above are merely illustrative and that aromatic hydrocarbons including aromatic hydrocarbons containing a non-polar substituent, may be alkylated or transalkylated in accordance with the present invention.

It will also be appreciated that the operating conditions for the alkylation or transalkylation reactions in accordance with the process of this invention, as exemplified in the foregoing examples, may be varied within the limits specified and that various modifications and alterations may be made in the process of this invention without departing from the spirit and scope thereof.

What is claimed is:

1. A process for effecting alkylation of an aromatic hydrocarbon charge selected from the group consisting of aromatic hydrocarbons and aromatic hydrocarbons containing a non-polar substituent which comprises contacting said hydrocarbon charge with an alkylating agent under conditions effective for accomplishing said alkylation including a reactor inlet temperature between about 100° F and about 1200° F, a reactor pressure between atmospheric and about 3000 psig, employing a mole ratio of hydrocarbon charge to alkylating agent in the approximate range of 1:3 to 20:1 and a weight hourly space velocity between about 0.5 and 1000 in the presence of a catalyst comprising a crystalline aluminosilicate zeolite, or a product of heating said zeolite to a temperature of from about 500° F to about 1500° F, characterized by the X-ray diffraction pattern of Table 1 and a formula, expressed in terms of mole ratios of oxides in the anhydrous state, as follows:

$$(0.3-2.5)R_2O:(0-0.8)M_2O:Al_2O_3: > 8SiO_2$$

wherein R is an organic nitrogen-containing cation derived from ethylenediamine or pyrrolidine and M is an alkali metal cation, said zeolite being further characterized, after calcination at 600° C, by exhibiting a sorption ratio of n-hexane/2-methylpentane of less than 10 at 90° C.

2. The process of claim 1 wherein the alkylating agent is an olefin.

3. The process of claim 2 wherein the reactor inlet temperature is between about 100° F and 950° F and the reactor pressure is between about 25 psig and 800 psig.

4. The process of claim 2 wherein the crystalline aluminosilicate zeolite or the product of heating said zeolite is characterized by a SiO$_2$:Al$_2$O$_3$ ratio between greater than 8 and about 50.

5. The process of claim 2 wherein the crystalline aluminosilicate zeolite or the product of heating said zeolite is combined in an amount between about 1 and about 99 weight percent in a binder therefor.

6. The process of claim 5 wherein said binder is alumina.

7. The process of claim 1 wherein the alkylating agent is an alcohol.

8. The process of claim 7 wherein the reactor inlet temperature is between about 400° F and 1200° F and the reactor pressure is between about 25 psig and 800 psig.

9. The process of claim 7 wherein the crystalline aluminosilicate zeolite or the product of heating said zeolite is characterized by a SiO$_2$:Al$_2$O$_3$ ratio between greater than 8 and about 50.

10. The process of claim 7 wherein the crystalline aluminosilicate zeolite or the product of heating said zeolite is combined in an amount between about 1 and about 99 weight percent in a binder therefor.

11. The process of claim 10 wherein said binder is alumina.

12. A process for effecting transalkylation of an aromatic hydrocarbon charge selected from the group consisting of aromatic hydrocarbons and aromatic hydrocarbons containing a non-polar substituent which comprises contacting said hydrocarbon charge with a transalkylating agent under conditions effective for accomplishing said transalkylation including a reactor inlet temperature between about 650° F and about 1100° F, a reactor pressure between atmospheric and about 3000 psig, employing a mole ratio of hydrocarbon charge to transalkylating agent in the approximate range of 1:3 to 20:1 and a weight hourly space velocity between about 0.5 and 1000 in the presence of a catalyst comprising a crystalline aluminosilicate zeolite, or a product of heating said zeolite to a temperature of from about 500° F to about 1500° F, characterized by the X-ray diffraction pattern of Table 1 and a formula, expressed in terms of mole ratios of oxides in the anhydrous state, as follows:

$$(0.3-2.5)R_2O:(0-0.8)M_2O:Al_2O_3: > 8SiO_2$$

wherein R is an organic nitrogen-containing cation derived from ethylenediamine or pyrrolidine and M is an alkali metal cation, said zeolite being further characterized, after calcination at 600° C, by exhibiting a sorption ratio of n-hexane/2-methylpentane of less than 10 at 90° C.

13. The process of claim 12 wherein the reactor pressure is between about 25 psig and 800 psig.

14. The process of claim 12 wherein the crystalline aluminosilicate zeolite or the product of heating said zeolite is characterized by a SiO$_2$:Al$_2$O$_3$ ratio between greater than 8 and about 50.

15. The process of claim 12 wherein the crystalline aluminosilicate zeolite or the product of heating said zeolite is combined in an amount between about 1 and about 99 weight percent in a binder therefor.

16. The process of claim 15 wherein said binder is alumina.

17. The process of claim 12 wherein the aromatic hydrocarbon charge is toluene and the transalkylating agent is trimethylbenzene.

18. The process of claim 12 wherein the aromatic hydrocarbon charge is toluene and the transalkylating agent is toluene.

19. A process for effecting alkylation of an aromatic hydrocarbon charge selected from the group consisting of aromatic hydrocarbons and aromatic hydrocarbons containing a non-polar substituent which comprises contacting said hydrocarbon charge with an alkylating agent under conditions effective for accomplishing said alkylation including a reactor inlet temperature between about 100° F and about 1200° F, a reactor pressure between atmospheric and about 3000 psig, employing a mole ratio of hydrocarbon charge to alkylating agent in the approximate range of 1:3 to 20:1 and a weight hourly space velocity between about 0.5 and 1000 in the presence of a catalyst comprising a crystalline aluminosilicate zeolite, or a product of heating said zeolite to a temperature of from about 500° F to about 1500° F, characterized by the X-ray diffraction pattern of Table 2 and a formula, expressed in terms of mole ratios of oxides in the anhydrous state, as follows:

$$(0.3-2.5)R_2O:(0-0.8)M_2O:Al_2O_3: > 8SiO_2$$

wherein R is an organic nitrogen-containing cation derived from a 2-(hydroxyalkyl) trialkylammonium compound and M is an alkali metal cation, said zeolite being further characterized, after calcination at 600° C, by exhibiting a sorption ratio of n-hexane/2-methylpentane of less than 10 at 90° C.

20. A process for effecting transalkylation of an aromatic hydrocarbon charge selected from the group consisting of aromatic hydrocarbons and aromatic hydrocarbons containing a non-polar substituent which comprises contacting said hydrocarbon charge with a transalkylating agent under conditions effective for accomplishing said transalkylation including a reactor inlet temperature between about 650° F and about 1100° F, a reactor pressure between atmospheric and about 3000 psig, employing a mole ratio of hydrocarbon charge to transalkylating agent in the approximate range of 1:3 to 20:1 and a weight hourly space velocity between about 0.5 and 1000 in the presence of a catalyst comprising a crystalline aluminosilicate zeolite, or a product of heating said zeolite to a temperature of from about 500° F to about 1500° F, characterized by the X-ray diffraction pattern of Table 2 and a formula, expressed in terms of mole ratios of oxides in the anhydrous state, as follows:

$$(0.3-2.5)R_2O:(0-0.8)M_2O:Al_2O_3: > 8SiO_2$$

wherein R is an organic nitrogen-containing cation derived from a 2-(hydroxyalkyl) trialkylammonium compound and M is an alkali metal cation, said zeolite being further characterized, after calcination at 600° C, by exhibiting a sorption ratio of n-hexane/2-methylpentane of less than 10 at 90° C.

21. The process of claim 19 wherein the alkylating agent is an olefin.

22. The process of claim 21 wherein the reactor inlet temperature is between about 100° F and 950° F and the reactor pressure is between about 25 psig and 800 psig.

23. The process of claim 21 wherein the crystalline aluminosilicate zeolite or the product of heating said zeolite is characterized by a $SiO_2:Al_2O_3$ ratio between greater than 8 and about 50.

24. The process of claim 21 wherein the crystalline aluminosilicate zeolite or the product of heating said zeolite is combined in an amount between about 1 and about 99 weight percent in a binder therefor.

25. The process of claim 24 wherein said binder is alumina.

26. The process of claim 19 wherein the alkylating agent is an alcohol.

27. The process of claim 26 wherein the reactor inlet temperature is between about 400° F and 1200° F and the reactor pressure is between about 25 psig and 800 psig.

28. The process of claim 26 wherein the crystalline aluminosilicate zeolite or the product of heating said zeolite is characterized by a $SiO_2:Al_2O_3$ ratio between greater than 8 and about 50.

29. The process of claim 26 wherein the crystalline aluminosilicate zeolite or the product of heating said zeolite is combined in an amount between about 1 and about 99 weight percent in a binder therefor.

30. The process of claim 29 wherein said binder is alumina.

31. The process of claim 20 wherein the reactor pressure is between about 25 psig and 800 psig.

32. The process of claim 20 wherein the crystalline aluminosilicate zeolite or the product of heating said zeolite is characterized by a $SiO_2:Al_2O_3$ ratio between greater than 8 and about 50.

33. The process of claim 20 wherein the crystalline aluminosilicate zeolite or the product of heating said zeolite is combined in an amount between about 1 and about 99 weight percent in a binder therefor.

34. The process of claim 33 wherein said binder is alumina.

35. The process of claim 20 wherein the aromatic hydrocarbon charge is toluene and the transalkylating agent is trimethylbenzene.

36. The process of claim 20 wherein the aromatic hydrocarbon charge is toluene and the transalkylating agent is toluene.

* * * * *

UNITED STATES PATENT AND TRADEMARK OFFICE
CERTIFICATE OF CORRECTION

PATENT NO. : 4,070,407
DATED : January 24, 1978
INVENTOR(S) : Werner O. Haag and David H. Olson It is certified that error appears in the above-identified patent and that said Letters Patent are hereby corrected as shown below:

Column 11, line 12, "$[(CH_3)_3\text{-n-}$" should read -- $[(CH_3)_3\text{-N-}$ --.

Signed and Sealed this

Twenty-ninth Day of August 1978

[SEAL]

Attest:

RUTH C. MASON
Attesting Officer

DONALD W. BANNER
Commissioner of Patents and Trademarks